United States Patent [19]

Honeybourne et al.

[11] Patent Number: 5,244,812
[45] Date of Patent: Sep. 14, 1993

[54] DETECTION OF ELECTRON ACCEPTOR GASES USING SULFUR-SELENIUM FULVALENES

[75] Inventors: Colin L. Honeybourne, Wotton-Under-Edge; Richard J. Ewen, Bristol, both of England

[73] Assignee: British Technology Group Limited, London, England

[21] Appl. No.: 800,517

[22] Filed: Dec. 3, 1991

[30] Foreign Application Priority Data

Dec. 6, 1990 [GB] United Kingdom .............. 9026544

[51] Int. Cl.$^5$ .............................................. G01N 21/01
[52] U.S. Cl. ..................................... 436/164; 422/88; 422/90; 422/91; 422/98; 436/106; 436/116; 436/117; 436/118; 436/124; 436/151
[58] Field of Search ........................ 549/35, 36, 39; 436/106, 116–118, 124, 151, 164; 422/88, 90, 91, 98

[56] References Cited

U.S. PATENT DOCUMENTS

| | | | |
|---|---|---|---|
| 2,942,952 | 6/1960 | Plantz .................... | 436/124 |
| 3,748,097 | 7/1973 | Lerner .................... | 436/124 |
| 3,779,814 | 12/1973 | Miles et al. ............. | 549/35 X |
| 3,977,831 | 8/1976 | Fletcher et al. .......... | 436/134 X |
| 4,028,346 | 6/1977 | Engler et al. ............ | 549/39 X |
| 4,032,297 | 6/1977 | Lyshkow ................... | 436/117 X |
| 4,236,307 | 12/1980 | Colla et al. ............. | 436/117 X |
| 4,246,173 | 1/1981 | Cowan et al. ............. | 549/35 X |
| 4,465,845 | 8/1984 | Okamoto et al. ........... | 549/35 X |
| 4,572,900 | 2/1986 | Wohltjen ................. | 422/94 X |
| 4,722,905 | 2/1988 | Honeybourne et al. ....... | 436/116 X |
| 4,871,680 | 10/1989 | Barraud et al. ........... | 436/124 X |

FOREIGN PATENT DOCUMENTS

132903 11/1978 Fed. Rep. of Germany ...... 436/118
1-172382 7/1989 Japan ..................... 549/36
2-152975 6/1990 Japan ..................... 549/39

OTHER PUBLICATIONS

Wudl, F. et al. "Electrical Conductivity by the Bis-1,-3-dithiole-Bis-1,3-Dithiolium System" *J. Am. Chem. Soc.* 1972, 94, 670–672.

Edward M. Engler "Organic Metals" *Chemical Technology*, 1976, 6, 274–279.

M. Narita et al, "Preparation of Tetrathiafulvalenes (TTF) and their Selenium Analogs-Tetraselenafulvalenes (TseF)" *Synthesis*, 1976, 489–514.

E. M. Engler "Synthesis of Tetrathiafulvalene Derivatives via Polymer-Bound Triphenylphosphine" IBM Technical Bulletin 1977, 19, 3925–3927.

T. Hanawa et al. "Gas Sensitivities of Polypyrrole Films to Electron Acceptor Gaes" *Bull. Chem. Soc. Jpn.*, 1989, 62, 1710–1714.

R. J. Ewen et al., "The Electrical Conductance of Thin Films of a new Class of Organic Semiconductor with Potential as a Detector of Electron Acceptor Gases" *Chemistry and Industry* 1982, 490–491.

W. Chen et al. "Synthesis of Bis(2,5-dimethylpyrrolo[3-,4-d]tetrathiafulvalene, an Annelated TTF Derivative with Good Electron Donor Properties". J. Am. Chem. Soc. 1988, 110, 7903–7904.

*Primary Examiner*—James C. Housel
*Assistant Examiner*—Arlen Soderquist
*Attorney, Agent, or Firm*—Nixon & Vanderhye

[57] ABSTRACT

$NO_2$ and other electron acceptor gases can be detected at 5 volume parts per million by tetrathiafulvalene TTF. The TTF may be incorporated in a polystyrene film, which changes its infra-red spectrum and conductivity upon exposure to such gases.

9 Claims, 3 Drawing Sheets

DETECTION OF ELECTRON ACCEPTOR GASES USING SULFUR-SELENIUM FULVALENES

This invention relates to the detection of electron acceptor gases, and in particular to the detection of nitrogen dioxide present, for example, with dinitrogen-tetroxide in NOX.

Equipment for the detection of specific gases such as NOX which depend on chemiluminescence or mass spectrometry tends to be bulky and/or weighty. The most promising method of detection which might enable a portable specific gas detector to be developed is infra-red spectrometry, particularly in view of the recent development of solid state infra-red sources such as light emitting diodes and solid state lasers.

At low concentrations of gas (usually up to 5 parts per million by volume), however, the path length through a gas necessary to produce measurable infra-red absorption would be so large as to prohibit the use of infra-red detection in a portable device.

Previously reported compounds, such as phthalocyanines and tetraazaannulenes have affinities for gases such as NOX and exhibit a greatly enhanced electrical conductivity when thin films thereof deposited on electrodes are exposed to the gas. At gas concentrations 5 vpm or less, however, these compounds do not exhibit measurable change in their infra-red spectrum.

Compounds have now been found which can be used to specifically detect a gas such as NOX by a specific change in the infra-red spectrum of a compound on exposure to a gas.

Accordingly, the present invention comprises the use in a detector of an electron acceptor gas of a compound of formula I:

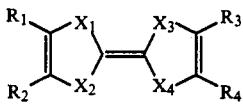

wherein
- $X_1 X_2 X_3$ and $X_4$, which may be identical or different, represent sulphur or selenium and
- $R_1 R_2 R_3$ and $R_4$, which may be identical or different, represent electron donating substituents, for example alkyl groups, (especially $C_1$-$C_6$ alkyl groups) or hydrogen.

It is generally preferred that $X_1$-$X_4$ represent sulphur and that $R_1$-$R_4$ represent hydrogen, the compound tetrathiafulvalene (TTF) being or particular interest.

Electron acceptor gases, such as nitrogen dioxide, chlorine, bromine, iodine, ozone and boron trifluoride are believed to form charge transfer complexes when exposed to compounds of formula I. Nitrogen dioxide, for example, is believed to form $TTF^+ NO_2^-$. Such complexes generally exhibit characteristics such as ultraviolet or visible spectrum or dark DC conductivity which are markedly distinct from the respective characteristics of the compound of formula I or electron acceptor gas per se. A readily measurable change in infra-red spectrum may not, however, take place when a compound of formula I is exposed to all electron acceptor gases. In the case of nitrogen dioxide, however, which is typically present in mixtures with dinitrogen tetroxide as NOX, absorption bands appear in the infra-red spectrum when a sample of compound I is exposed to the gas, in the case of TTF in the regions 805–835 and 1720–1420 cm$^{-1}$ such as at 1358 cm$^{-1}$ ($\pm 5$ cm$^{-1}$). The appearance of such bands is regarded as characteristic of the presence of nitrogen dioxide in the gas and can be readily detected. Detection of nitrogen dioxide in a gas sample may, if desired, be accompanied by quantitative determination using electronic measurements on the same sample. The compound of formula I may be incorporated into a film of e.g. polymer for ease of use and ease of measurement.

In a further aspect of the present invention a method of detecting an electron acceptor gas comprises exposing a compound of formula I to the gas whereby a change takes place in a measurable characteristic of the compound and detecting said change.

The invention also extends to a detector operating by this method. The present invention may be carried into effect variously. A monitor may for example comprise a badge 2 to be worn by those liable to be exposed to an environment in which an electron acceptor gas requires monitoring. The badge 2 may comprise a compound of formula I carried e.g. as a film 4 on a suitable support 6, whereby exposure to the gas give rise to an optically detectable colour change e.g. from yellow to purple. The compound I may be conveniently supported on cellulosic material for example, by dipping the material in a solution of the compound and allowing it to dry or compounds may be incorporated in a polymer presented to the gas in the form of a film. Such a colour change integrates exposure to gas, i.e. the same colour change would be produced by a short exposure to a high concentration of gas as to a relatively long exposure to a low concentration.

Specific monitoring of nitrogen dioxide (e.g. in NOX) in the presence of other electron acceptor gases may be achieved by detecting the change in the infra-red absorption in the regions 805–835 and 1270–1420 cm$^{-1}$ or in other parts of the infra-red spectrum produced on exposure, for example by analysis of the badge.

It is envisaged that chlorine, for example, can be detected in the presence of NOX by determination of the differences in UV and/or visible spectrum produced on uptake by a compound I of chlorine relative to NOX, coupled if desired with utilisation of the change in infra-red spectrum given by NOX but not by chlorine uptake.

If appropriate, the electrical conductance may also be monitored and coupled to an alerting system.

Such a device is useful only until the compound I is spent by exposure to the gas, but it is possible to minimise this possible drawback by utilising a support for compound I which has a very high surface area/volume ratio, such as a tape, and containing the support within a small volume, for example, in the case of tape, in a cassette, the support being driven continuously or intermittently past a window allowing exposure to the electron acceptor gas. The support and exposed compound I would be analysed at intervals for uptake of gas or might be subject to continuous detection of gas uptake by infra-red and/or conductivity measuring gleans incorporated in the monitoring device.

If desired the badge hereinbefore described can incorporate means for detecting a change in electrical conductance of the compound I coupled to means for alerting the user when the conductance represents a harmful level of gas. The badge may for example, comprise electrodes, and a power source coupled to an audible alarm.

A continuous monitoring device may comprise an infra-red source and detector tuned to an infra-red band which exhibits a marked change on exposure of the compound I to the electron acceptor gas (for example 805-835 cm$^{-1}$ and/or 1270-1420 cm$^{-1}$ in the case of NOX and TTF), there being interposed between source and detector an amount of compound I sufficient to produce a detectable change in infra-red absorption. The detector would generally be coupled to means for alerting the user to the presence of the gas.

BRIEF DESCRIPTION OF THE DRAWINGS

The invention will be further described with reference to the accompanying drawings, in which.

Figure 1:
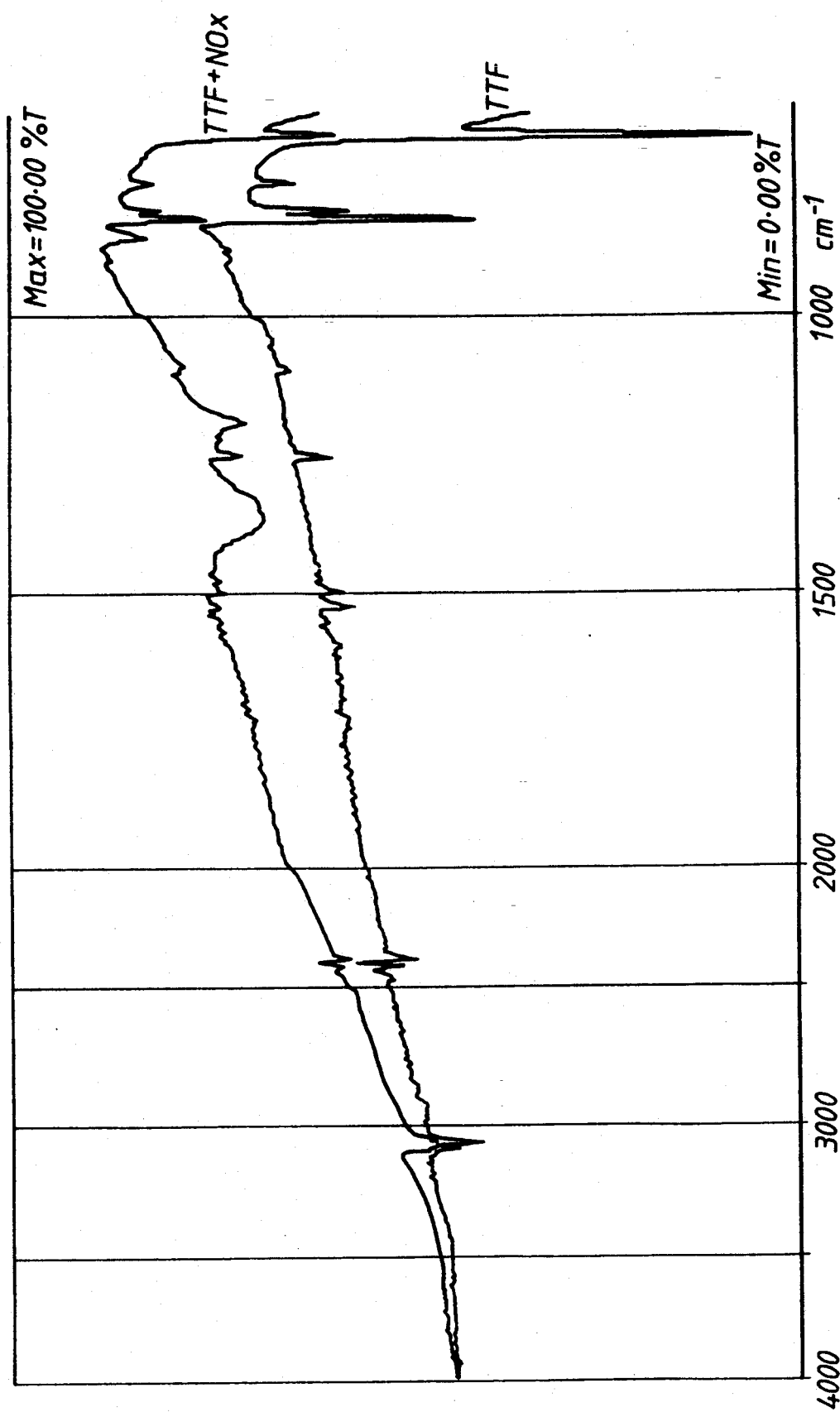
FIG. 1 is an infrared spectrum of TTF before and after uptake of NOX.

The infra-red spectrum of TTF before and after uptake of NOX is shown in FIG. 1 of the accompanying drawings, the TTF having been deposited from solution in CHCl$_3$ onto a disc of NaCl.

Figure 2:
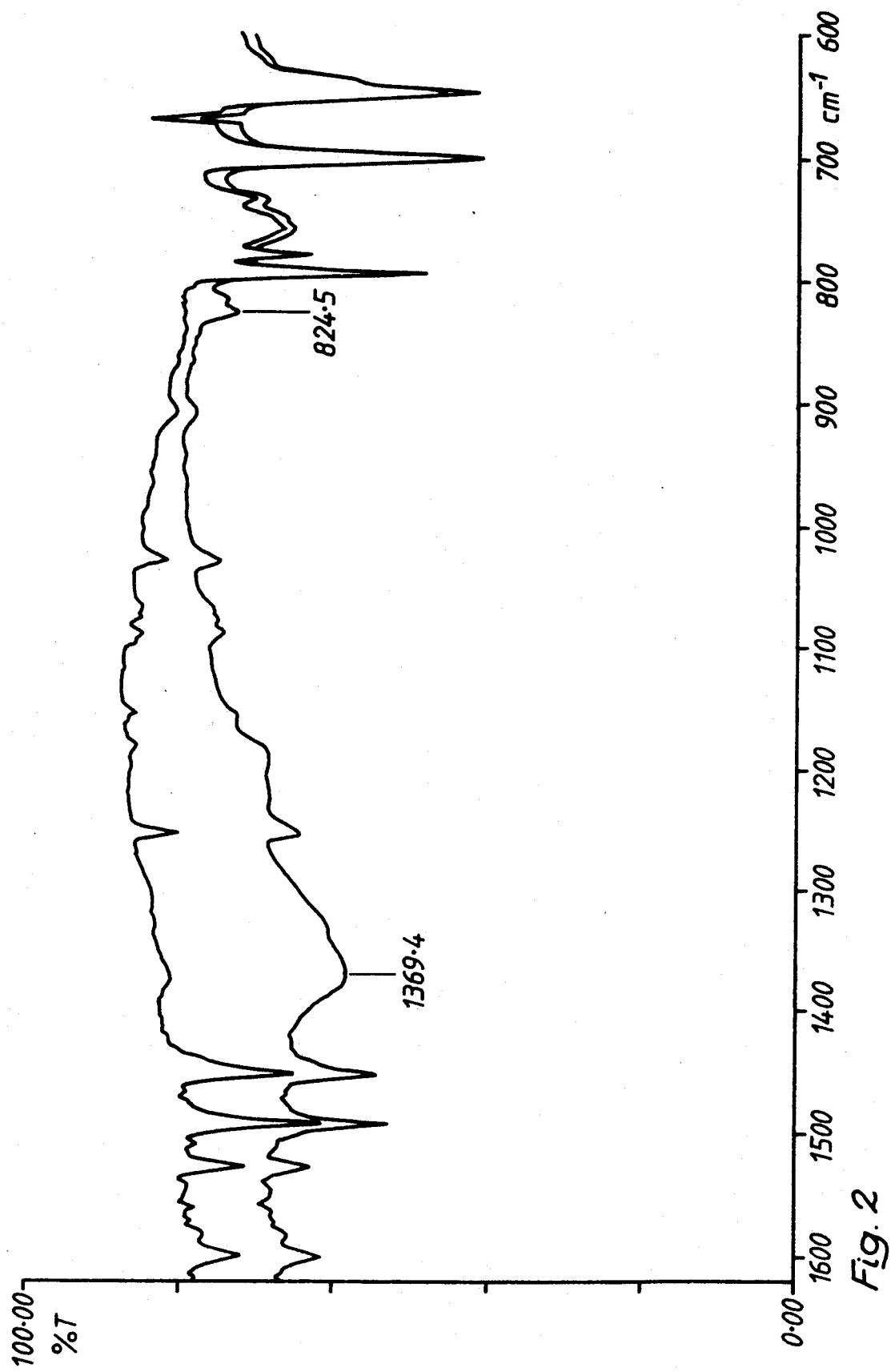
FIG. 2 is an infrared spectrum of a 5-micron TTF-polystyrene film before and after 15 minutes exposure to 5 volume parts per million of NO$_x$.
Figure 3:
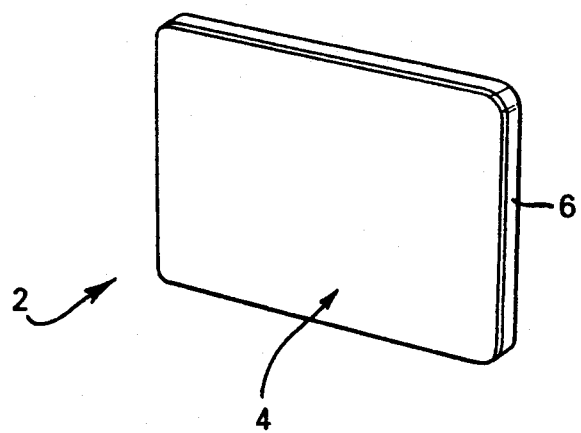
FIG. 3 show a device of the invention.

FIG. 2 of the accompanying drawings shows the infra-red spectrum of a 5-micron TTF-polystyrene film before (upper (higher transition) curve) and after 15 minute's exposure (lower curve) to 5 volume parts per million of NO$_x$. The film was made by allowing drops of chloroform CHCl$_3$, containing as solute equal masses of TTF and polystyrene, to spread on the surface of water and allowing the chloroform to evaporate. Polymethylmethacrylate in place of the polystyrene gave similar results.

In another example, a TTF-polystyrene film (1:1 by weight) was deposited similarly to the above from one drop of chloroform onto an alumina base carrying interdigitated platinum electrodes held at a potential difference of 10 V, for establishing film conductivity. On stepwise exposure of the film to 5 volume parts per million, the current rose from an initial $3.3 \times 10^{-8}$ A to $5.0 \times 10^{-4}$ A over the course of 10 minutes.

We claim:

1. A method of detecting an electron acceptor gas comprising exposing to the gas a compound of formula I:

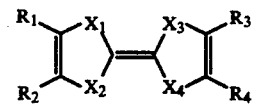

wherein $X_1$, $X_2$, $X_3$ and $X_4$, which may be the same or different, are S or Se, and wherein $R_1$, $R_2$, $R_3$ and $R_4$, which may be the same or different, are electron-donating substituents, whereby a change takes place in the spectral absorption of the compound, and detecting said change.

2. A method according to claim 1, wherein $R_1$, $R_2$, $R_3$ and $R_4$, which may be the same or different, are alkyl groups or hydrogen.

3. A method according to claim 2, wherein the alkyl groups are $C_1$-$C_6$.

4. A method according to claim 1, wherein $X_1=X_2=X_3=X_4=S$.

5. A method according to claim 1, wherein $R_1=R_2=R_3=R_4=H$.

6. A method according to claim 1, wherein a change in the electrical conductivity is also detected.

7. A method according to claim 1, wherein nitrogen dioxide is the electron acceptor gas.

8. A method according to claim 1, wherein chlorine is the electron acceptor gas.

9. A method according to claim 1, wherein nitrogen dioxide and chlorine are detected in each other's presence.

* * * * *